United States Patent
Liew (10) Patent No.: US 11,447,772 B2
(45) Date of Patent: Sep. 20, 2022

(54) MIRNA AS BIOMARKER FOR PARKINSON'S DISEASE AND DIAGNOSTIC KIT USING SAME

(71) Applicant: KOOKMIN UNIVERSITY INDUSTRY ACADEMY COOPERATION FOUNDATION, Seoul (KR)

(72) Inventor: Hyunjeong Liew, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 113 days.

(21) Appl. No.: 16/631,954

(22) PCT Filed: Jul. 17, 2018

(86) PCT No.: PCT/KR2018/008085
§ 371 (c)(1),
(2) Date: Jun. 26, 2020

(87) PCT Pub. No.: WO2019/017680
PCT Pub. Date: Jan. 24, 2019

(65) Prior Publication Data
US 2020/0332290 A1 Oct. 22, 2020

(30) Foreign Application Priority Data

| Jul. 19, 2017 | (KR) | 10-2017-0091417 |
| Sep. 12, 2017 | (KR) | 10-2017-0116583 |
| Oct. 12, 2017 | (KR) | 10-2017-0132866 |
| Oct. 12, 2017 | (KR) | 10-2017-0132867 |
| Oct. 12, 2017 | (KR) | 10-2017-0132868 |
| Oct. 12, 2017 | (KR) | 10-2017-0132869 |
| Oct. 12, 2017 | (KR) | 10-2017-0132870 |

(51) Int. Cl.
| C12N 15/113 | (2010.01) |
| C12Q 1/6883 | (2018.01) |
| A61P 25/28 | (2006.01) |
| A61K 9/00 | (2006.01) |

(52) U.S. Cl.
CPC .......... *C12N 15/113* (2013.01); *A61K 9/0056* (2013.01); *A61P 25/28* (2018.01); *C12Q 1/6883* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 4,437,975 A | 3/1984 | Gillespie et al. |
| 4,683,195 A | 7/1987 | Mullis et al. |
| 4,683,202 A | 7/1987 | Mullis |
| 4,800,159 A | 1/1989 | Mullis et al. |
| 4,988,617 A | 1/1991 | Landergren et al. |
| 5,242,794 A | 9/1993 | Whiteley et al. |
| 5,494,810 A | 2/1996 | Barany et al. |
| 6,410,276 B1 | 6/2002 | Burg et al. |
| 6,582,938 B1 | 6/2003 | Su et al. |
| 9,297,007 B2 | 3/2016 | Reijerkerk et al. |
| 2012/0172416 A1 | 7/2012 | Velin |
| 2014/0134728 A1 | 5/2014 | Henrion-Caude |
| 2015/0166959 A1 | 6/2015 | Paek |
| 2015/0275299 A1 | 10/2015 | Xu |
| 2017/0009295 A1 | 1/2017 | Rigoutsos |
| 2017/0044529 A1 | 2/2017 | Ruohola-Baker et al. |
| 2017/0226587 A1* | 8/2017 | Mounier .............. C12Q 1/6883 |
| 2019/0249250 A1 | 8/2019 | Bianco |

FOREIGN PATENT DOCUMENTS

| CN | 106434939 | 2/2017 |
| EP | 0329822 | 8/1989 |
| EP | 0439182 | 7/1991 |
| EP | 2757157 | 7/2014 |
| KR | 1020100104930 | 9/2010 |
| KR | 101305515 | 9/2013 |
| WO | 88/10315 | 12/1988 |
| WO | 89/06700 | 7/1989 |
| WO | 90/01069 | 2/1990 |
| WO | 90/06995 | 6/1990 |
| WO | 2014018650 | 1/2014 |
| WO | 2014/075822 | 5/2014 |
| WO | 2014075822 | 5/2014 |

(Continued)

OTHER PUBLICATIONS

Taguchi et al. Cells 7, 245, pp. 1-8 (Year: 2018).*
Xiong, R., et al., "MicroRNA-494 reduces DJ-1 expression and exacerbates neurodegeneration," Neurobiology of Aging 35 (2014); 705-714.
Margis, R., et al., "Identification of blood microRNAs associated to Parkinson's Disease," Journal of Biotechnology 152 (2011); 96-101.
Kim et al., "Integrative Analysis of Differential Gene Expression and DNA Methylation of Ethylbenzene-exposed Workers", BioChip J., 2015, vol. 9, Issue 3, pp. 259-267.

(Continued)

*Primary Examiner* — Brian Whiteman
(74) *Attorney, Agent, or Firm* — Duane Morris LLP; Gregory M. Lefkowitz; Brandon A. Chan (57) ABSTRACT

The present invention relates to a method for providing information on the diagnosis of Parkinson's disease. The present invention also relates to a composition for preventing, ameliorating or treating Parkinson's disease. The present invention uses at least one miRNA whose expression is specifically down- or up-regulated in a Parkinson's disease model. Therefore, the use of the miRNA is effective in diagnosing and treating Parkinson's disease.

4 Claims, 5 Drawing Sheets

Specification includes a Sequence Listing.

(56) References Cited

FOREIGN PATENT DOCUMENTS

| WO | WO-2016020626 A1 * | 2/2016 | ........... C12Q 1/6883 |
|---|---|---|---|
| WO | WO-2016029260 A1 * | 3/2016 | ........... C12Q 1/6886 |
| WO | 2017/084770 | 5/2017 | |
| WO | 2017084770 | 5/2017 | |

OTHER PUBLICATIONS

Jeong et al., "MicroRNA microarray analysis of human umbilical vein endothelial cells exposed to benzo(a)pyrene", BioChip J., 2012, vol. 6, Issue 2, pp. 191-196.

Cho et al., "A relationship between MiRNA and gene expression in the mouse Sertoli cell line after exposure to biosphenol A", BioChip J., 2010, vol. 4, Issue 1, pp. 75-81.

Chandrasekaran et al., "A Network View on Parkinson's Disease", Computational and Structural Biotechnology Journal, Apr. 2013, vol. 7, Issue 8, e201304004.

Park et al., "Expression profiles of miRNAs during ethanol-induced differentiation of neural stem cells", BioChip J., 2012, vol. 6, Issue 1, pp. 73-83.

Park et al., "Functional Screening of Altered MicroRNA Expression in 3-methylcholanthrene-treated Human Umbilical Vein Endothelial Cells", BioChip J., 2014, vol. 8, Issue 4, pp. 260-268.

Lee et al., "Identification and Characterization of MicroRNAs in Acrolein-Stimulated Endothelial Cells: Implications for Vascular Disease", BioChip J., 2015, DOI 10.1007/s13206-015-9303-3.

Song, K.H., et al., "Sho-saiko-to, a traditional herbal medicine, regulate gene expression and biological function by way of microRNAs in primary mouse hepatocytes," BMC Complementary and Alternative Medicine, 2014, 14:14.

* cited by examiner

[Fig. 1]

| Index | Probe Set ID | Transcript ID (miRNA name) | Accession | log ratio [W vs. C] | FCAbsolute [W vs. C] | Regulation [W vs. C] |
|---|---|---|---|---|---|---|
| 436 | 20503803 | hsa-miR-494-3p | MIMAT0002818 | -3.024323 | 8.136018728 | down |
| 898 | 20506835 | hsa-miR-1244 | MIMAT0005896 | -2.68516 | 6.431521165 | down |
| 2207 | 20525497 | hsa-miR-6768-5p | MIMAT0027436 | -2.33117 | 5.032132814 | down |
| 1198 | 20517704 | hsa-miR-4324 | MIMAT0016876 | -2.119451 | 4.34528559 | down |
| 1740 | 20519566 | hsa-miR-4726-5p | MIMAT0019843 | -2.045094 | 4.127001607 | down |
| 510 | 20503877 | hsa-miR-501-5p | MIMAT0002872 | -2.019869 | 4.055525878 | down |

[Fig. 2]

| Index | Probe Set ID | Transcript ID (miRNA name) | Accession | log ratio [W vs. C] | FCAbsolute [W vs. C] | Regulation [W vs. C] |
|---|---|---|---|---|---|---|
| 843 | 20506767 | hsa-miR-1226-5p | MIMAT0005576 | 2.117824 | 4.340387954 | up |
| 1816 | 20519642 | hsa-miR-4767 | MIMAT0019913 | 1.996284 | 3.989710318 | up |
| 1759 | 20519585 | hsa-miR-3064-5p | MIMAT0019864 | 1.962058 | 3.896173707 | up |

MIRNA AS BIOMARKER FOR PARKINSON'S DISEASE AND DIAGNOSTIC KIT USING SAME

CROSS-REFERENCE TO RELATED APPLICATIONS

This application is a § 371 national stage entry of International Application No. PCT/KR2018/008085, filed on Jul. 17, 2018, which claims priority to Korean Patent Application No. 10-2017-0091417, filed on Jul. 19, 2017, Korean Patent Application No. 10-2017-0116583, filed on Sep. 12, 2017, Korean Patent Application No. 10-2017-0132866, filed on Oct. 12, 2017, Korean Patent Application No. 10-2017-0132867, filed on Oct. 12, 2017, Korean Patent Application No. 10-2017-0132868, filed on Oct. 12, 2017, Korean Patent Application No. 10-2017-0132869, filed on Oct. 12, 2017, and Korean Patent Application No. 10-2017-0132870, filed on Oct. 12, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 25, 2020, is named G1035-15901 RevisedSequenceList.txt and is 1,893 bytes in size.

TECHNICAL FIELD

The present invention relates to a method for diagnosing Parkinson's disease using at least one miRNA whose expression is down- or up-regulated in Parkinson's disease and a composition for preventing or treating Parkinson's disease using the miRNA.

BACKGROUND ART

Parkinson's disease is a degenerative disease of the central nervous system. Parkinson's disease starts from the degeneration of neurons in the substantia nigra pars compacta of the midbrain and its pathophysiological symptoms include reduced brain volume and aggregation of α-synuclein (αSyn). This disease is accompanied by gait disturbance, hand tremor, and rigidity.

The number of patients with Parkinson's disease in Korea had increased by an average annual growth of 8.7% from 61,565 in 2010 to 85,588 in 2014. The proportion of patients over the age of 60 in 2014 was 95.7%. The prevalence of Parkinson's disease correlates with the age of patients. The numbers of male and female patients with Parkinson's disease in 2014 were 33,831 and 52,057, respectively (see "Increases in the number and medical expense of patients with Parkinson's disease for recent 5 years", The Korean Doctor's Weekly, 2015).

The population of patients with Parkinson's disease in seven major countries (including the United States, Japan, France, Germany, Italy, Spain, and the United Kingdom) had increased by an average annual growth of 2.72% from 4.54 million in 2008 to 5.05 million in 2012. The population of patients with Parkinson's disease in Asian countries had grown from 1.95 million in 2008 to 2.19 million in 2012. The population of patients with Parkinson's disease in European countries had grown from 0.82 million in 2008 to 0.91 million in 2012 (Product and Pipeline Analysis of the Global Parkinson's Disease Therapeutic Market, F&S, 2014).

Following the recent trend of therapeutic agents for Parkinson's disease, dopamine agonist drugs accounted for the largest share (47%) of the global market in 2011 but are estimated to decrease to 42% in 2021, and instead, novel pipeline drugs are predicted to account for approximately 20% in 2021 (R&D Trends: Parkinson's Disease, Datamonitor, 2012).

The subject is diagnosed with Parkinson's disease by various examinations, including 1) PET, 2) MRI, and 3) examinations for internal diseases.

Dopamine transporter positron emission tomography (PET) is an examination for determining whether dopaminergic cells are damaged. PET can be used to detect parkinsonian symptoms caused by factors other than Parkinson's disease. Drug-induced parkinsonian syndromes, vascular parkinsonian syndromes, parkinsonian symptoms associated with Alzheimer's disease, and parkinsonian symptoms associated with essential tremor are often accompanied by tremor and bradykinesia similar to parkinsonian symptoms but are characterized by normal dopaminergic neurons.

It is important to distinguish Parkinson's disease from similar diseases with parkinsonian symptoms. Magnetic resonance imaging (MRI) of the brain is required to distinguish Parkinson's disease from secondary parkinsonian syndromes and atypical parkinsonian syndromes. Patients with Parkinson's disease have normal MRI results but diseases other than Parkinson's disease exhibit characteristic MRI features.

Examinations for internal diseases (blood, urine, electrocardiogram, and mammogram examinations) to diagnose Parkinson's disease are conducted to determine the onset and progression of other internal diseases that are often mistaken for parkinsonian symptoms while causing systemic weakness.

However, these diagnostic methods for Parkinson's disease involve high cost and complex processes. Lundbeck, one of the leading companies focused on the treatment and diagnosis of Parkinson's disease, mentioned the importance of the development of tools for rapid diagnosis of Parkinson's disease on its homepage but does not currently sell commercial reagents or kits. Further, the number of patients afflicted with Parkinson's disease has been increasing sharply over the years and the market for therapeutic agents for Parkinson's disease have rapidly grown in proportion thereto. However, the market for diagnostics for Parkinson's disease is currently in an at the early stage of development. Thus, there is an urgent need to develop a technique for distinguishing Parkinson's disease from its similar diseases to rapidly and economically diagnose Parkinson's disease and a technique for treating Parkinson's disease simultaneously with the diagnosis of Parkinson's disease.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The present inventors have earnestly and intensively conducted research to develop a technique for distinguishing Parkinson's disease from its similar diseases to rapidly and economically diagnose Parkinson's disease and a technique for treating Parkinson's disease simultaneously with the diagnosis of Parkinson's disease, and as a result, found that a specific increase or decrease in the expression level of a specific miRNA in a Parkinson's disease model can be used for efficient diagnosis and treatment of Parkinson's disease. The present invention has been accomplished based on this finding.

Therefore, one object of the present invention is to provide a method for providing information on the diagnosis of Parkinson's disease.

A further object of the present invention is to provide a kit for diagnosing Parkinson's disease or analyzing the prognosis of Parkinson's disease.

Another further object of the present invention is to provide a method for screening a substance causing Parkinson's disease.

Another object of the present invention is to provide a method for screening a therapeutic agent for Parkinson's disease.

Another object of the present invention is to provide a composition for preventing, ameliorating or treating Parkinson's disease.

Still another object of the present invention is to provide a method for treating Parkinson's disease.

Other objects and advantages of the invention become more apparent from the following detailed description, claims, and drawings.

Means for Solving the Problems

One aspect of the present invention provides a method for providing information on the diagnosis of Parkinson's disease including (a) comparing the expression level of at least one miRNA selected from the group consisting of miR-494-3p, miR-501-5p, miR-1244, miR-6768-5p, miR-4324, and miR-4726-5p present in a sample taken from a subject with that of the selected miRNA in a normal sample and (b) diagnosing the subject with Parkinson's disease when the expression level of the selected miRNA in the subject sample is lower than that of the selected miRNA in the normal sample.

According to a preferred embodiment of the present invention, the method further includes (a) comparing the expression level of at least one miRNA selected from the group consisting of miR-1226-5p, miR-4767, and miR-3064-5p in a sample taken from a subject with that of the selected miRNA in a normal sample and (b) diagnosing the subject with Parkinson's disease when the expression level of the selected miRNA in the subject sample is higher than that of the selected miRNA in the normal sample.

A further aspect of the present invention provides a method for providing information on the diagnosis of Parkinson's disease including (a) comparing the expression level of at least one miRNA selected from the group consisting of miR-1226-5p, miR-4767, and miR-3064-5p in a sample taken from a subject with that of the selected miRNA in a normal sample and (b) diagnosing the subject with Parkinson's disease when the expression level of the selected miRNA in the subject sample is higher than that of the selected miRNA in the normal sample.

The term "miRNA" as used herein is used to intend a 15-25 base non-coding RNA that is transcribed as a RNA precursor having a hairpin-like structure, cleaved by a dsRNA-cleaving enzyme having RNase III cleavage activity, incorporated into a protein complex, called RISC, and involved in the suppression of mRNA translation, unless otherwise specified. The term "miRNA" as used herein is intended to include not only a miRNA represented by a particular nucleotide sequence (or SEQ ID NO) but also a precursor of the miRNA (pre-miRNA or pri-miRNA) and miRNAs having biological functions equivalent thereto, for example, congeners (i.e. homologs or orthologs), variants (e.g., genetic polymorphs), and derivatives. Such precursors, congeners, variants or derivatives can be specifically identified using miRBase Release 20 (www.mirbase.org), and examples thereof include miRNAs having sequences hybridizing with the sequences complementary to the sequences set forth in SEQ ID Nos. 1 to 9 under stringent conditions. The term "miRNA" as used herein may be a gene product of a miR gene. Such a gene product includes a mature miRNA (e.g., a 15-25 base or 19-25 base non-coding RNA involved in the suppression of mRNA translation as described above) or a miRNA precursor (e.g., pre-miRNA or pri-miRNA as described above).

The term "nucleic acid" as used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA, and synthetic RNA. The terms "synthetic DNA" and the "synthetic RNA" as used herein refer to DNA and RNA that are artificially produced on the basis of predetermined sequences (which may be any of natural and non-natural sequences), for example, using an automatic nucleic acid synthesizer. The term "non-natural sequence" as used herein is intended to be used in a broad sense and includes, for example, a sequence including substitution, deletion, insertion, and/or addition of one or more nucleotides (i.e. a variant sequence) and a sequence including one or more modified nucleotides (i.e. a modified sequence), which are different from the natural sequence. The term "polynucleotide" as used herein is used interchangeably with the term "nucleic acid".

The term "subject" as used herein is interpreted as having a meaning including mammals such as primates, including humans and chimpanzees, household pets, including dogs and cats, livestock, including cattle, horses, sheep, and goats, and rodents, including mice and rats. The term "normal group" as used herein is interpreted as having the same meaning as the term "subject" and refers to an object unaffected with Parkinson's disease to be detected.

The sample is not limited as long as it is naturally or artificially isolated from the subject and contains genetic information associated with Parkinson's disease of the subject. The sample is preferably isolated from feces, cells, blood, plasma, serum, hair or urine. The sample is more preferably a blood, plasma or serum sample isolated from the body.

The diagnostic method of the present invention can use various tests known in the art. Examples of such tests include, but are not limited to, hybridization, immunoassay, and gene amplification.

The hybridization uses a probe to identify the presence of the miRNA.

The term "probe" as used herein refers to a natural or modified monomer or a linkage of linear oligomers. The probe is intended to include deoxyribonucleotides and ribonucleotides, can specifically hybridize with a target nucleotide sequence, and naturally occurs or is artificially synthesized. The probe is preferably single-stranded and an oligodeoxyribonucleotide.

The diagnostic method of the present invention can be carried out by hybridization using a microarray. In this case, the probe is used as a hybridizable array element and is immobilized on a substrate. The substrate is preferably a rigid or semi-rigid support and examples thereof include membranes, filters, chips, slides, wafers, fibers, magnetic or non-magnetic beads, gels, tubing, plates, polymers, microparticles, and capillaries. The hybridizable array element is arrayed and immobilized on the substrate. This immobilization is accomplished by chemical bonding or covalent bonding, for example, by UV. For example, the hybridizable array element may be bound to a glass surface modified so as to include an epoxy compound or an aldehyde group and may also be bound to a polylysine-coated surface by UV. Alternatively, the hybridizable array element may be bound to the substrate via linkers (e.g., an ethylene glycol oligomer and a diamine).

A sample DNA used in the microarray is optionally labeled and is hybridized with the array element on the microarray. The hybridization can be performed under various conditions. The degree of hybridization can be detected and analyzed by various techniques depending on the labeling material.

The labeling of the probe can provide a signal that can be used to detect whether hybridization takes place or not and the labeled probe can be linked to an oligonucleotide. Suitable labels include, but are not limited to, fluorophores (e.g., fluorescein, phycoerythrin, rhodamine, lissamine, and Cy3 and Cy5 (Pharmacia)), terminal deoxynucleotidyl transferase (TdT), chemoluminophores, magnetic particles, radioisotopes ($P^{32}$ and $S^{35}$), mass labels, electron-dense particles, enzymes (alkaline phosphatase or horseradish peroxidase), cofactors, substrates for enzymes, heavy metals (e.g., gold), and haptens having specific binding partners such as antibodies, streptavidin, biotin, digoxigenin, and chelating groups. The labeling can be performed by various techniques known in the art, such as nick translation, random priming (Multiprime DNA labeling systems booklet, "Amersham" (1989)), and kination (Maxam & Gilbert, Methods in Enzymology, 65: 499 (1986)). The signal provided by the labeling can be detected by fluorescence, radioactivity, colorimetry, gravimetry, X-ray diffraction or absorption, magnetism, enzymatic activity, mass analysis, binding affinity, hybridization, high frequency or nanocrystals.

The probe is hybridized with cDNA molecules. Suitable hybridization conditions can be determined through a series of processes by an optimization procedure. This procedure is performed through a series of processes by one skilled in the art to establish protocols for laboratory use. For example, conditions such as temperature, concentration of components, hybridization and washing times, buffer components and their pH, and ionic strength may vary depending on various factors such as length and GC content of the probe and the sequence of the target nucleotide. Specific hybridization conditions can be found in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999).

The resulting hybridization signal is detected. The hybridization signal may be detected by various methods depending on the label bound to the probe. For example, when the probe is labeled with an enzyme, the substrate of the enzyme is allowed to react with the hybridization product to determine whether hybridization takes place. Examples of available enzyme/substrate combinations include: combinations of peroxidases (e.g., horseradish peroxidase) and chloronaphtol, aminoethylcarbazole, diaminobenzidine, D-luciferin, lucigenin (bis-N-methylacridinium nitrate), resorufin benzyl ether, luminol, Amplex Red reagent (10-acetyl-3,7-dihydroxyphenoxazine), p-phenylenediamine-HCl and pyrocatechol (HYR), tetramethylbenzidine (TMB), 2,2'-azino-di(3-ethylbenzthiazoline sulfonate) (ABTS), o-phenylenediamine (OPD), and naphthol/pyronine; combinations of alkaline phosphatase and bromochloroindolyl phosphate (BCIP), nitroblue tetrazolium (NBT), naphthol-AS-BT-phosphate, and ECF; and combinations of glucosidase and t-nitroblue tetrazolium (t-NBT) and m-phenazine methosulfate (m-PMS). The probe can be labeled with gold particles. In this case, the signal may be detected by silver staining using silver nitrate.

The subject is diagnosed with Parkinson's disease when the hybridization signal for the sequence of the miRNA in the biological sample is up- or down-regulated compared to that in the normal sample.

The diagnostic method of the present invention may be carried out by immunoassay. The immunoassay is intended to include radioimmunoassay, radioimmunoprecipitation, immunoprecipitation, enzyme-linked immunosorbent assay (ELISA), capture-ELISA, inhibition or competition assay, sandwich immunoassay, flow cytometry, immunofluorescent staining, and immunoaffinity purification, but is not limited thereto. These immunoassay techniques are described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, which are incorporated herein by reference.

The diagnostic method of the present invention may be carried out by gene amplification. The detection of the miRNA by gene amplification may be performed by various techniques known in the art. In this case, primers or a probe may be used for the miRNA.

The expression level of the miRNA gene is investigated by gene amplification with primers. Since the diagnostic method of the present invention is based on the analysis of the expression level of the gene, the quantity of mRNA in the marker in the analyte sample (e.g., cells) is investigated to determine the expression level of the marker gene. Accordingly, gene amplification is in principle performed using mRNA as a template in the biological sample and primers binding to the mRNA or cDNA.

First, total RNA is isolated from the sample to obtain mRNA. This isolation can be accomplished by any suitable method known in the art (see Sambrook, J. et al., Molecular Cloning. A Laboratory Manual, 3rd ed. Cold Spring Harbor Press (2001); Tesniere, C. et al., Plant Mol. Biol. Rep., 9:242 (1991); Ausubel, F. M. et al., Current Protocols in Molecular Biology, John Willey & Sons (1987); and Chomczynski, P. et al., Anal. Biochem. 162:156 (1987)). For example, Trizol may be used to easily isolate total RNA from cells.

Subsequently, cDNA is synthesized from the isolated mRNA and is then amplified. Since the total RNA is isolated from the human sample, it has a poly-A tail at the end of the mRNA. Based on such sequence characteristics, cDNA can be easily synthesized using oligo dT primers and a reverse transcriptase (see PNAS USA, 85:8998 (1988); Libert F, et al., Science, 244:569 (1989); and Sambrook, J. et al., Molecular Cloning. A Laboratory Manual, 3rd ed. Cold Spring Harbor Press (2001)). Then, the synthesized cDNA is amplified by gene amplification. The primers used in the present invention are hybridized with or annealed to one site of the template to form a double-chain structure. Suitable nucleic acid hybridization conditions for forming the double-chain structure are disclosed in Joseph Sambrook, et al., Molecular Cloning, A Laboratory Manual, Cold Spring Harbor Laboratory Press, Cold Spring Harbor, N.Y. (2001), and Haymes, B. D., et al., Nucleic Acid Hybridization, A Practical Approach, IRL Press, Washington, D.C. (1985).

Various DNA polymerases can be used for amplification in the present invention. Such DNA polymerases include "Klenow" fragment of *E. coli* DNA polymerase I, thermostable DNA polymerases, and bacteriophage T7 DNA polymerase. Specifically, the polymerase is a thermostable DNA polymerase that can be obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu). When the polymerization reaction is performed, it is preferable to provide a reaction container with excess amounts of components necessary for the reaction. The excess amount of each of the components necessary for the amplification reaction means an amount such that the amplification reaction is not substantially limited by the concentration of the component. It is desirable to provide cofactors such as $Mg^{2+}$, and dATP, dCTP, dGTP, and dTTP to the reaction mixture in such amounts that the desired degree of amplification can be achieved. All enzymes used for the amplification reaction may be active under the same reaction conditions. In fact, the use of a buffer allows all enzymes to approach optimal reaction conditions. Therefore, the amplification can be performed in a single reactant without changing the conditions, such as addition of other reactants.

The annealing or hybridization is performed under strict conditions that allow specific binding between the target nucleotide sequence and the primers. The strict conditions for the annealing are sequence-dependent and vary depending on the surrounding environmental variables.

The term "amplification" as used herein refers to a reaction for amplifying nucleic acid molecules. A variety of amplification reactions have been reported in the art, and examples thereof include polymerase chain reaction (PCR, U.S. Pat. Nos. 4,683,195, 4,683,202, and 4,800,159), reverse transcription-polymerase chain reaction (RT-PCR, Sambrook et. al., Molecular Cloning. A Laboratory Manual, 3rd ed. Cold Spring Harbor Press (2001)), Miller, H. I. (WO 89/06700) and Davey, C. et. al., (EP 329,822), multiplex PCR (McPherson and Moller, 2000), ligase chain reaction (LCR) (17, 18), Gap-LCR (WO 90/01069), repair chain reaction (EP 439,182), transcription-mediated amplification (TMA) (19) (WO 88/10315), self sustained sequence replication (20) (WO 90/06995), selective amplification of target polynucleotide sequences (U.S. Pat. No. 6,410,276), consensus sequence primed polymerase chain reaction (CP-PCR, U.S. Pat. No. 4,437,975), and loop-mediated isothermal amplification (LAMP), but are not limited thereto. Other available amplification methods are disclosed in U.S. Pat. Nos. 5,242,794, 5,494,810, and 4,988,617, and U.S. patent application Ser. No. 09/854,317.

PCR is the most well-known method for nucleic acid amplification and many modifications and applications thereof have been developed. For example, touchdown PCR, hot start PCR, nested PCR, and booster PCR have been developed by modifying traditional PCR procedures for the purpose of enhancing the specificity or sensitivity of PCR. Real-time PCR, differential display PCR (DD-PCR), rapid amplification of cDNA ends (RACE), multiplex PCR, inverse polymerase chain reaction (IPCR), vectorette PCR, and thermal asymmetric interlaced PCR (TAIL-PCR) have been developed for specific applications. Details of PCR are described in McPherson, M. J., and Moller, S. G. PCR. BIOS Scientific Publishers, Springer-Verlag New York Berlin Heidelberg, N.Y. (2000), the disclosure of which is incorporated by reference herein.

The primers used for gene amplification in the present invention are oligonucleotides that have sequences complementary to the cDNA sequence of the miRNA. As used herein, the term "primer" refers to a single-stranded oligonucleotide that can act as a starting point for template-directed DNA synthesis at a suitable temperature under suitable conditions in a suitable buffer (i.e. four different nucleoside triphosphates and polymerases). The length of each primer may vary depending on various factors, for example, temperature and the application of the primer, but the primer typically has 15 to 35 nucleotides A low temperature is generally required such that a short primer molecule forms a sufficiently stable hybrid complex with the template.

The sequences of the primers do not have to be completely complementary to a portion of the sequence of the template and are not limited as long as the primers are sufficiently complementary to the template for hybridization with the template to perform their inherent functions. The sequence of the primer set used in the present invention does not have to be completely complementary to the cDNA sequence of the marker as the template and is not limited as long as the primer set is sufficiently complementary to the template for hybridization with the template to perform their inherent functions. Preferably, the primers used in the present invention have sequences completely complementary to the cDNA sequence of the marker.

The primers can be easily designed by one skilled in the art with reference to the cDNA sequence of the miRNA. For example, the PRIMER 3 program may be used for primer design.

The cDNA of the amplified marker is analyzed by a suitable method to investigate the expression level of the marker gene. For example, the amplification product is subjected to gel electrophoresis and the resulting bands are observed and analyzed to investigate the expression level of the marker gene.

The subjected is diagnosed with Parkinson's disease when the expression of the gene in the biological sample is up- or down-regulated compared to that in the normal sample after the amplification.

The miRNA is a biomolecule whose expression is down- or up-regulated in Parkinson's disease. As used herein, the term "high expression (or overexpression)" or "up-regulation" means that the expression level of the target nucleotide sequence or protein in the biological sample is high compared to that in the normal sample. For example, this term means that the expression is up-regulated when analyzed by a method commonly used in the art, for example, RT-PCR or ELISA (see Sambrook, J. et al., Molecular Cloning. A Laboratory Manual, 3rd ed. Cold Spring Harbor Press (2001)). For example, when the expression of the miRNA is up- or down-regulated by 10% compared to that in the normal sample, as analyzed by the diagnostic method, the subject is diagnosed with Parkinson's disease.

In the Examples section that follows, the expression of the miRNA was found to be up- or down-regulated by at least 10%, preferably at least 50% in a patient with Parkinson's disease compared to in a healthy subject.

Another aspect of the present invention provides a kit for diagnosing Parkinson's disease or analyzing the prognosis of Parkinson's disease including a nucleic acid capable of specific binding to at least one miRNA selected from the group consisting of miR-494-3p, miR-501-5p, miR-1244, miR-6768-5p, miR-4324, miR-4726-5p, miR-1226-5p, miR-4767, and miR-3064-5p.

According to a preferred embodiment of the present invention, the kit of the present invention further includes a nucleic acid capable of specific binding to at least one miRNA selected from the group consisting of hsa-miR-494-3p, hsa-miR-1244, hsa-miR-6768-5p, hsa-miR-4324, hsa-miR-4726-5p, hsa-miR-501-5p, hsa-miR-1226-5p, hsa-miR-4767, and hsa-miR-3064-5p.

In addition to the nucleic acid, the kit of the present invention may include a nucleic acid known in the art or a nucleic acid that is likely to be developed in the future for the detection of Parkinson's disease. The kit of the present invention may also include a known antibody for measuring the marker for Parkinson's disease.

The nucleic acids of the kit according to the present invention may be packaged individually or in any combination in different containers.

The kit of the present invention may include a kit for extracting a nucleic acid (for example, total RNA) from body fluids, cells or tissues, a fluorescent material for labeling, an enzyme and medium for nucleic acid amplification, and/or instructions for use.

The kit of the present invention is a device for measuring the marker for Parkinson's disease. For example, the nucleic acid is bound or attached to a solid in the kit of the present invention. Examples of materials for the solid include plastics, paper, glass, and silicone. For ease of processing, the solid is preferably made of a plastic material. The solid may be arbitrary in shape, for example, quadrangular, circular or rectangular, or may be in the form of a film.

The kit of the present invention may include a nucleic acid capable of specific binding to at least one miRNA, preferably at least two miRNAs, more preferably at least three miRNAs.

Another aspect of the present invention provides a method for screening a substance causing Parkinson's disease including (i) treating cells expressing at least one miRNA selected from the group consisting of miR-494-3p, miR-501-5p, miR-1244, miR-6768-5p, miR-4324, and miR-4726-5p with a candidate substance causing Parkinson's disease and quantifying the expression level of the selected miRNA in the treated cells and (ii) determining the candidate substance to cause Parkinson's disease when the expression of the selected miRNA in the treated cells is down-regulated.

According to a preferred embodiment of the present invention, the screening method of the present invention may further include (i) treating cells expressing at least one miRNA selected from the group consisting of miR-1226-5p, miR-4767, and miR-3064-5p with a candidate substance causing Parkinson's disease and quantifying the expression level of the selected miRNA in the treated cells and (ii) determining the candidate substance to cause Parkinson's disease when the expression of the selected miRNA in the treated cells is up-regulated.

Another aspect of the present invention provides a method for screening a substance causing Parkinson's disease including (i) treating cells expressing at least one miRNA selected from the group consisting of miR-1226-5p, miR-4767, and miR-3064-5p with a candidate substance causing Parkinson's disease and quantifying the expression level of the selected miRNA in the treated cells and (ii) determining the candidate substance to cause Parkinson's disease when the expression of the selected miRNA in the treated cells is up-regulated.

Another aspect of the present invention provides a method for screening a therapeutic agent for Parkinson's disease including (i) treating cells expressing at least one miRNA selected from the group consisting of miR-494-3p, miR-501-5p, miR-1244, miR-6768-5p, miR-4324, and miR-4726-5p with a candidate therapeutic agent for Parkinson's disease and quantifying the expression level of the selected miRNA in the treated cells and (ii) determining the candidate therapeutic agent to treat Parkinson's disease when the expression of the selected miRNA in the treated cells is up-regulated.

According to a preferred embodiment of the present invention, the screening method of the present invention further includes (i) treating cells expressing at least one miRNA selected from the group consisting of miR-1226-5p, miR-4767, and miR-3064-5p with a candidate therapeutic agent for Parkinson's disease and quantifying the expression level of the selected miRNA in the treated cells and (ii) determining the candidate therapeutic agent to treat Parkinson's disease when the expression of the selected miRNA in the treated cells is down-regulated.

Another aspect of the present invention provides a method for screening a therapeutic agent for Parkinson's disease including (i) treating cells expressing at least one miRNA selected from the group consisting of miR-1226-5p, miR-4767, and miR-3064-5p with a candidate therapeutic agent for Parkinson's disease and quantifying the expression level of the selected miRNA in the treated cells and (ii) determining the candidate therapeutic agent to treat Parkinson's disease when the expression of the selected miRNA in the treated cells is down-regulated.

The term "candidate" used while mentioning the screening methods of the present invention refers to an unknown substance (for example, a natural substance, compound library, gene or protein library) used for screening to determine whether it is active in causing, alleviating, preventing or relieving parkinsonian symptoms.

As used herein, the term "therapeutic agent for Parkinson's disease" refers to a drug (or a pharmaceutical composition), a health functional food or a diet that is known or found to be pharmacologically active against Parkinson's disease. For example, the use of a drug and functional food whose pharmacological activity against Parkinson's disease is known in the art enables the diagnosis of the sensitivity of a subject diagnosed with Parkinson's disease or the prediction of the prognosis of Parkinson's disease. As another example, the methods of the present invention can be applied to screening of substances having pharmacological activity against Parkinson's disease from candidates whose pharmacological activities against Parkinson's disease are unknown.

Another aspect of the present invention provides a composition for preventing, ameliorating or treating Parkinson's disease including, as an active ingredient, at least one miRNA selected from the group consisting of miR-494-3p, miR-501-5p, miR-1244, miR-6768-5p, miR-4324, and miR-4726-5p.

Yet another aspect of the present invention provides a method for treating Parkinson's disease including administering to a patient an effective amount of at least one miRNA selected from the group consisting of miR-494-3p, miR-501-5p, miR-1244, miR-6768-5p, miR-4324, and miR-4726-5p.

According to one embodiment of the present invention, the composition may be a pharmaceutical composition.

The pharmaceutical composition of the present invention may include a pharmaceutically acceptable carrier. The pharmaceutically acceptable carrier of the pharmaceutical composition according to the present invention may be any of those known in the art. Examples of carriers suitable for use in the pharmaceutical composition of the present invention include, but are not limited to, lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. The pharmaceutical composition of the present invention may further include at least one additive selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences (19th ed., 1995).

The pharmaceutical composition of the present invention can be administered orally or parenterally. For parenteral administration, the pharmaceutical composition of the present invention may be administered nasally, ophthalmically, intravenously, subcutaneously, intramuscularly, intraperitoneally or transdermally.

A suitable dosage of the pharmaceutical composition according to the present invention may vary depending on various factors such as formulation method, mode of administration, age, body weight, sex, and pathological condition of the patient, diet, time and route of administration, rate of excretion, and responsiveness. A physician having ordinary skill in the art can readily determine and prescribe a desired therapeutically or prophylactically effective amount of the pharmaceutical composition. According to a preferred embodiment of the present invention, the daily dose of the pharmaceutical composition according to the present invention is from 0.001 to 100 mg/kg.

The pharmaceutical composition of the present invention can be prepared in unit dosage forms or dispensed in multi-dose containers with a pharmaceutically acceptable carrier and/or excipient by a suitable method which can be easily carried out by one having ordinary skill in the art. The pharmaceutical composition of the present invention may be in the form of a solution, suspension or emulsion in an oil or aqueous medium. The pharmaceutical composition of the present invention may be in the form of an extract, powder, granule, tablet or capsule. The pharmaceutical composition of the present invention may further include a dispersant or a stabilizer.

The composition of the present invention can be formulated into skin preparations for external use, aerosols, sprays, eye drops, oral preparations, and injectable preparations.

According to one embodiment of the present invention, the composition may be a food composition.

The food composition of the present invention may optionally further include one or more ingredients that are usually added for food production. For example, the optional ingredients may be selected from proteins, carbohydrates, fats, nutrients, seasoning agents, and flavoring agents. Examples of the carbohydrates include: saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. Natural flavoring agents, such as thaumartin and stevia extracts (e.g., rebaudioside A and glycyrrhizin) and synthetic flavoring agents (e.g., saccharin and aspartame) may be used.

For example, the food composition of the present invention may be prepared into a drink. In this case, the food composition of the present invention may further include citric acid, high fructose corn syrup, sugar, glucose, acetic acid, malic acid, fruit juice, eucommia extract, jujube extract, licorice extract, etc.

Effects of the Invention

The features and advantages of the present invention are summarized as follows:

(i) The present invention provides a method for providing information on the diagnosis of Parkinson's disease.

(ii) The present invention provides a composition for preventing, ameliorating or treating Parkinson's disease.

(iii) The expression of the miRNA used in the present invention is specifically down- or up-regulated in a Parkinson's disease model. Therefore, the use of the miRNA is effective in diagnosing and treating Parkinson's disease.

BEST MODE FOR CARRYING OUT THE INVENTION

The present invention will be explained in more detail with reference to the following examples. It will be evident to those skilled in the art that the scope of the present invention is not limited by these examples according to the gist of the present invention.

EXAMPLES

Materials and Methods

1. SH-SY5Y Cell Culture

C57BL/6 SH-SY5Y neuroblast cells were cultured in Dulbecco's Modified Eagle's Medium (DMEM, Invitrogen, MD, USA) supplemented with 10% heat-inactivated fetal bovine serum (GIBCO, MD, USA) in a humidified 5% $CO_2$ chamber at 37° C. (Jang, S.-W., Oh, M.-S., Yang, S. I. & Cho, E.-M. Gene expression profiles of human neuroblastoma cells exposed to CuO nanoparticles and Cu ions. *BioChip Journal* 10, 140-149 (2016)). 6-Hydroxydopamine (Sigma-Aldrich, St. Louis, Mo., USA) was dissolved in phosphate buffered saline (PBS) and stored at −80° C. before use. Whenever necessary, the solution was plated and used as a batch reagent. Special care was taken because the solution was sensitive to light.

2. Cell Viability Test

Cell viability was observed using stable tetrazolium salt (WST-1 assay, Sigma-Aldrich, St. Louis, Mo., USA). SH-SY5Y cells were plated in each well of a 96-well plate at a density of 5000 cells/well and treated with 6-hydroxydopamine (6OHDA, 25 μM, 24 h). The test group was compared with a control group treated with PBS only. 2 h before completion of the experiment, WST-1 solution was added in an amount of 10 μl/well and cells were cultured in a chamber at 37° C. After completion of the experiment, a color change at 450 nm was observed.

3. RNA Isolation

Total RNA of the SH-SY5Y cell line treated with 6OHDA (25 μM, 24 h) was isolated using Trizol reagent. This procedure was performed according to the method recommended by the manufacturer (Invitrogen, California, USA). The quantity and purity of the isolated total RNA were monitored using a NanoDrop ND-2000 spectrophotometer (Nano Drop, Delaware, USA) at 260/280 nm (ratio 1.8-2.0) ratio (Kim, G. W. e. a. Integrative analyses of differential gene expression and DNA methylation of ethylbenzene-exposed workers. *BioChip Journal* 9, 259-267 (2015)).

4. miRNA Expression Profiling

Affymetrix miRNA 4.0 array (Lee, S. E. e. a. Identification and characterization of MicroRNAs in acrolein-stimulated endothelial cells: Implications for vascular disease. *BioChip Journal* 9, 144-155 (2015)) was used for miRNA expression profiling assay. The microarray data were analyzed using the Gene Expression Omnibus (GEO) database.

5. Target Prediction and Gene Ontology Analysis

Target miRNA genes were predicted utilizing TargetScan6.2 DB based on the miRNA expression profiles according to the miRanda algorithm (Kim, G. W. et al. Integrative analyses of differential gene expression and DNA methylation of ethylbenzene-exposed workers. *BioChip Journal* 9, 259-267 (2015)). The most frequent target miRNAs whose expression levels were high were reconfirmed using Gene Ontology (GO) categories (www.geneontology.org/) (Cho, H. et al. A relationship between miRNA and gene expression in the mouse Sertoli cell line after exposure to bisphenol A. *BioChip Journal* 4, 75-81 (2010); Jeong, S. I. et al. MicroRNA microarray analysis of human umbilical vein endothelial cells exposed to benzo(a)pyrene. *BioChip Journal* 6, 191-196 (2012); Park, H. R., Lee, S. E., Yang, H., Son, G. W. & Park, Y. S. Functional screening of altered microRNA expression in 3-methylcholanthrene-treated human umbilical vein endothelial cells. *BioChip Journal* 8, 260-268 (2014); Park, J. H. et al. Expression profiles of miRNAs during ethanol-induced differentiation of neural stem cells. *BioChip Journal* 6, 73-83 (2012)). The miRs were sorted in the order of increasing or decreasing expression level based on the $\log_2$ fold change.

6. Construction of Parkinson's Disease Animal Models 30 min before injection of 6-OHDA (Sigma, St. Louis, USA), desipramine (12.5 mg/kg; Sigma, St. Louis, USA), a noradrenalin transporter blocker, was injected intraperitoneally into experimental animals such that the toxicity of 6-OHDA affected dopaminergic neurons only. After each experimental animal was deeply anesthetized with intraperitoneal injection of a mixture of ketamine (40 mg/kg) and xylazine (5 mg/kg). Thereafter, the animal was fixed to a brain stereotactic apparatus (David KOPF instrument, CA, USA) under inhalation anesthesia and the scalp was excised to expose the skull. After the bregma was identified, small holes were formed at spots located 1.1 mm posterior and 1.2 mm lateral (right) to this landmark by using a dental drill. A 26-gauge needle was inserted to reach a point located 5.0 mm on the back through the hole such that it was placed on the medial forebrain bundle (MFB). 2 μL of a solution of 6-OHDA in 0.1% ascorbic acid (2.5 μg/μL) was injected at a rate of 0.5 μL/min through a 5 μL Hamilton syringe using an infusion pump (Harvard Apparatus., USA). 5 μL of the test miRNA was injected at a rate of 0.5 μL/min through another 5 μL Hamilton syringe. 5 min after completion of the injection, the Hamilton syringes were removed and the skin was sutured. The left hemisphere was not injected with the test substance ("internal control"). After the experimental animal was anesthetized with a mixture of ketamine (70 mg/kg) and xylazine (8 mg/kg), the animal was perfused with 4% paraformaldehyde (in 0.1 M phosphate buffer, pH 7.4) through the heart, followed by fixing. The brain tissue was excised.

Figure 1:
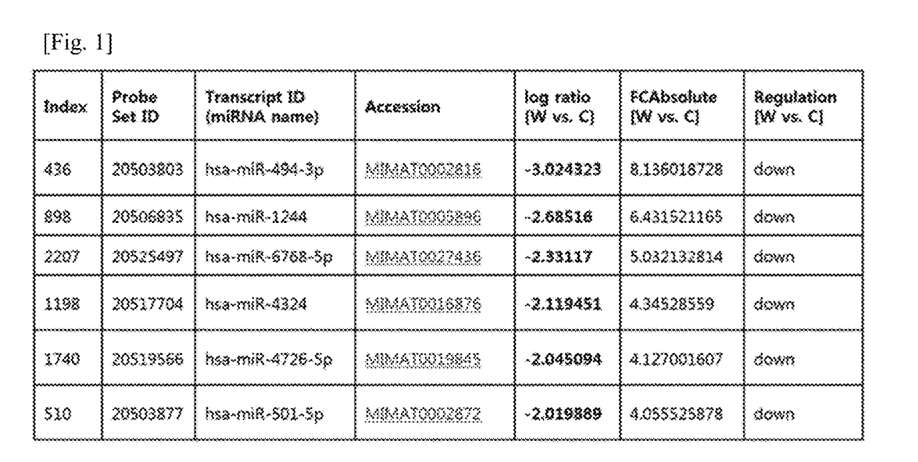
FIG. 1 shows miRNAs whose expression was down-regulated during apoptosis of cells in Parkinson's disease models.

Results 1. miRs Whose Expression was Down-Regulated During Apoptosis of Cells in the PD Models FIG. 1 shows miRNAs whose expression was most highly down-regulated during apoptosis of cells in the PD models. Particularly, it has not been reported that miR494-3p is associated with Parkinson's disease. A significant decrease in the expression level of miR494-3p was repeatedly observed in every experiment. miRs whose expression was down-regulated by ≤−2.0 (by ≥30%) based on the log ratio are also listed in FIG. 1. Particularly, bioinformatic data analysis revealed that miR-1244 targets the protein 'TBC1 domain family member 2B'. Importantly, the miRNA acts as a fundamental regulator that targets one of the genes specifically expressed during apoptosis of neurons in Parkinson's disease (A Network View on Parkinson's Disease, *Comput Struct Biotechnol J.* 2013; 7: e201304004).

Figure 2:
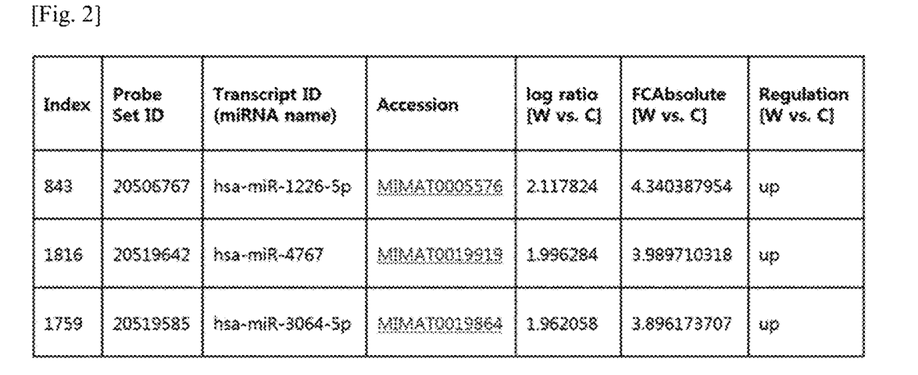
FIG. 2 shows miRNAs whose expression was up-regulated during apoptosis of cells in Parkinson's disease models.
Figure 3:
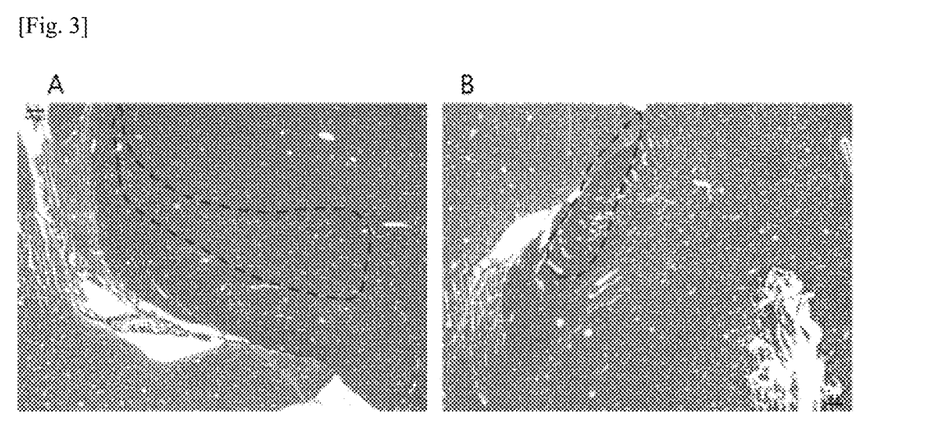
FIG. 3 shows images of an internal control injected with 6-OHDA. The substantia nigra of the left hemisphere of the brain whose tissue was untreated was left intact (A) and neurons of the substantia nigra of the right hemisphere injected with 6-hydroxydopamine were dead and their tissue was deformed, resulting in excessive shrinkage (B).
Figure 4:
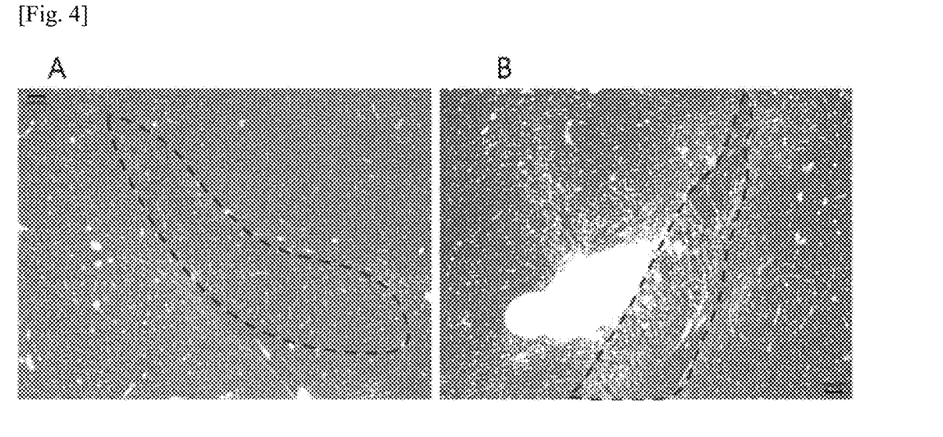
FIG. 4 shows living neurons in the substantia nigra under the influence of miR-494-3p co-injected with 6-OHDA. Lesions in A (normal) and B (injected) in the same individual were confirmed by H&E staining.
Figure 5:
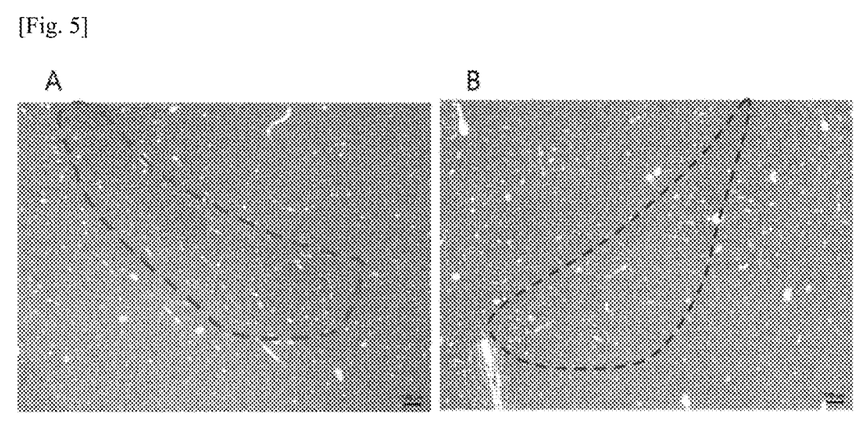
FIG. 5 shows living neurons in the substantia nigra under the influence of miR-1244 co-injected with 6-OHDA. Lesions in A (normal) and B (injected) in the same individual were confirmed by H&E staining.
Figure 6:
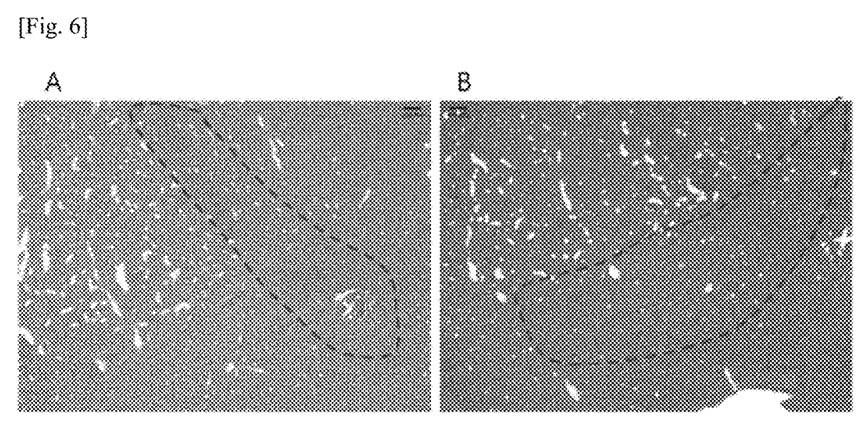
FIG. 6 shows living neurons in the substantia nigra under the influence of miR-4324 co-injected with 6-OHDA. Lesions in A (normal) and B (injected) in the same individual were confirmed by H&E staining.
Figure 7:
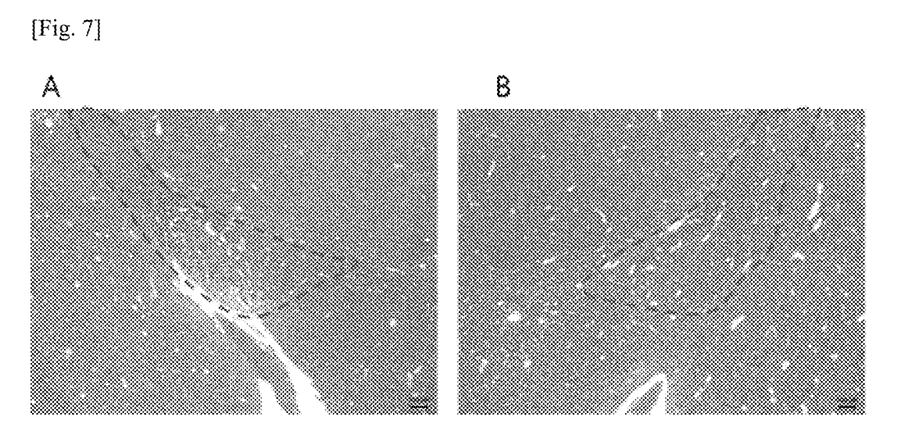
FIG. 7 shows living neurons in the substantia nigra under the influence of miR-4726-5p co-injected with 6-OHDA. Lesions in A (normal) and B (injected) in the same individual were confirmed by H&E staining.
Figure 8:
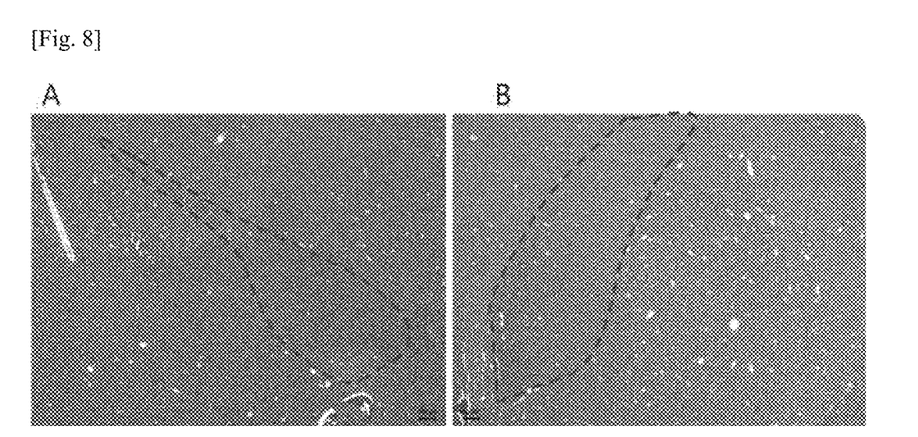
FIG. 8 shows living neurons in the substantia nigra under the influence of miR-6768-5p co-injected with 6-OHDA. Lesions in A (normal) and B (injected) in the same individual were confirmed by H&E staining.

2. miRs Whose Expression was Up-Regulated During Apoptosis of Cells in the PD Models FIG. 2 shows miRNAs whose expression was most highly up-regulated during apoptosis of cells in the PD models.

3. miR SEQ

The sequences of the miRNAs whose expression was highly up- or down-regulated are as follows:

The miRNAs whose expression was most highly down-regulated during apoptosis of cells in the PD models are hsa-miR-494-3p (SEQ ID NO. 1: UGAAACAUACACGG-GAAACCUC), hsa-miR-1244 (SEQ ID NO. 2: AAGUAGUUGGUUUGUAUGAGAUGGUU), hsa-miR-6768-5p (SEQ ID NO. 3: CACACAG-GAAAAGCGGGGCCCUG), hsa-miR-4324 (SEQ ID NO. 4: CCCUGAGACCCUAACCUUAA), hsa-miR-4726-5p (SEQ ID NO. 5: AGGGCCAGAGGAGCCUGGAGUGG), and hsa-miR-501-5p (SEQ ID NO. 6: AAUCCUUUGUCC-CUGGGUGAGA).

The miRNAs whose expression was most highly up-regulated during apoptosis of cells in the PD models are hsa-miR-1226-5p (SEQ ID NO. 7: GUGAGGG-CAUGCAGGCCUGGAUGGGG), hsa-miR-4767 (SEQ ID NO. 8: CGCGGGCGCUCCUGGCCGCCGCC), and hsa-miR-3064-5p (SEQ ID NO. 9: UCUGGCUGUUGUGGU-GUGCAA).

4. H&E Staining

Cell viabilities in the Substantia nigra pars compacta, where major lesions of Parkinson's disease arise, were confirmed by H&E staining and compared to evaluate the efficacy of the miRNAs against Parkinson's disease.

1) Tissue fixing: Cellular enzymes were inactivated and ingredients in the tissue were converted to insoluble states by coagulation or precipitation. The tissue was fixed by immersion in a fixing solution at 4° C. for at least one day such that the cellular structure was well preserved.

2) Dehydration and cleaning: Water was removed and solvents used for water removal were removed for easy penetration of paraffin into the sub-tissue.

3) Construction of paraffin block: The inner and outer portions of the tissue were shaped with paraffin without causing any deformation of the tissue and cellular structure.

4) Slide preparation: The paraffin block was sliced with a microtome knife into 10 μm thick continuous coronal sections to prepare silane coating slides.

5) Staining: After the treatment, the paraffin was removed for tissue preservation, the cell nuclei were stained with Harris hematoxylin. Eosin Y was used for contrast staining.

6) Cells were colored indigo blue and contrast-stained sections were colored pink.

5. Inhibitory Effect of the miRNAs on Neuronal Apoptosis

Figure 9:
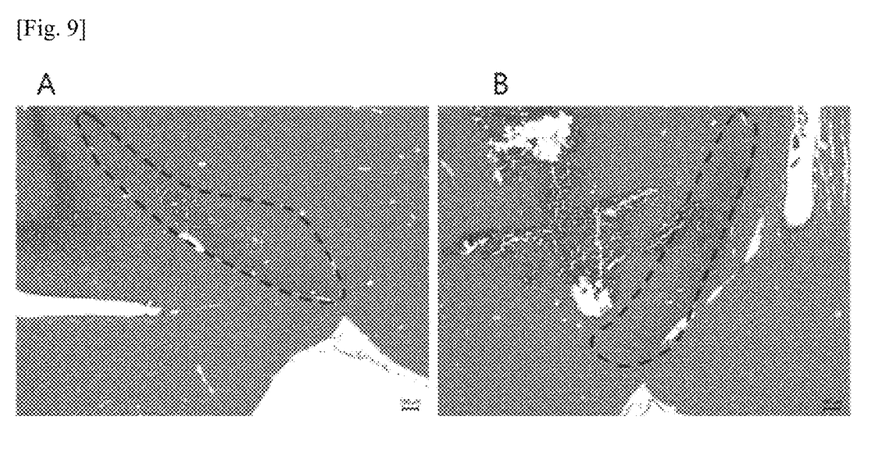
FIG. 9 shows living neurons in the substantia nigra under the influence of miR-501-5p co-injected with 6-OHDA. Lesions in A (normal) and B (injected) in the same individual were confirmed by H&E staining.

As can be seen from FIGS. 3 to 9, excessive shrinkage of the tissue was observed due to tissue deformation as well as neuronal apoptosis and in the internal control injected with 6-OHDA only (FIG. 3), whereas neurons were alive in the experimental groups received miR-494-3p (FIG. 4), miR-1244 (FIG. 5), miR-4324 (FIG. 6), miR-4726-5p (FIG. 7), miR-6768-5p (FIG. 8), and miR-501-5p (FIG. 9). These results demonstrated that the miRNAs are very effective in protecting neurons from apoptosis.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

The invention claimed is:

1. A method for providing information on the diagnosis of Parkinson's disease by determination of up-regulation of expression level of at least one miRNA in a blood, serum, or plasma sample taken from a subject comprising (a) comparing the expression level of at least one miRNA selected from the group consisting of miR-1226-5p and miR-3064-5p in the blood, serum, or plasma sample taken from the subject with that of the selected miRNA in a normal sample, and (b) diagnosing the subject with Parkinson's disease when the expression level of the selected miRNA is higher than that of the selected miRNA in the normal sample.

2. The method of claim 1, wherein the miRNA is miR-1226-5p.

3. The method of claim 1, wherein the miRNA is miR-3064-5p.

4. The method of claim 1, wherein the miRNA is miR-1226-5p and miR-3064-5p.

* * * * *

SEQUENCE LISTING

```
<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
ugaaacauac acgggaaacc uc                                              22

<210> SEQ ID NO 2
<211> LENGTH: 26
<212> TYPE: RNA
<213> ORGANISM: Homo sapiens

<400> SEQUENCE: 2
aaguaguugg uuuguaugag augguu                                          26

<210> SEQ ID NO 3
<211> LENGTH: 23
<212> TYPE: RNA
<213> ORGANISM: Homo sapiens

<400> SEQUENCE: 3
cacacaggaa aagcggggcc cug                                             23

<210> SEQ ID NO 4
<211> LENGTH: 20
<212> TYPE: RNA
<213> ORGANISM: Homo sapiens

<400> SEQUENCE: 4
cccugagacc cuaaccuuaa                                                 20

<210> SEQ ID NO 5
<211> LENGTH: 23
<212> TYPE: RNA
<213> ORGANISM: Homo sapiens
```

```
<400> SEQUENCE: 5
agggccagag gagccuggag ugg                                          23

<210> SEQ ID NO 6
<211> LENGTH: 22
<212> TYPE: RNA
<213> ORGANISM: Homo sapiens

<400> SEQUENCE: 6
aauccuuugu cccuggguga ga                                           22

<210> SEQ ID NO 7
<211> LENGTH: 26
<212> TYPE: RNA
<213> ORGANISM: Homo sapiens

<400> SEQUENCE: 7
gugagggcau gcaggccugg augggg                                       26

<210> SEQ ID NO 8
<211> LENGTH: 23
<212> TYPE: RNA
<213> ORGANISM: Homo sapiens

<400> SEQUENCE: 8
cgcgggcgcu ccuggccgcc gcc                                          23

<210> SEQ ID NO 9
<211> LENGTH: 21
<212> TYPE: RNA
<213> ORGANISM: Homo sapiens

<400> SEQUENCE: 9
ucuggcuguu guggugugca a                                            21
```